United States Patent
Urbanski et al.

(10) Patent No.: US 9,271,818 B2
(45) Date of Patent: Mar. 1, 2016

(54) CONICAL VENA CAVA FILTER WITH JUGULAR OR FEMORAL RETRIEVAL

(71) Applicant: Cook Medical Technologies LLC, Bloomington, IN (US)

(72) Inventors: Jason C. Urbanski, Bloomington, IN (US); Lindsay Koren, Bloomington, IN (US); Susan Kaiser, Neubiberg (DE); Thomas W. Jensen, Ballerup (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 171 days.

(21) Appl. No.: 13/776,635

(22) Filed: Feb. 25, 2013

(65) Prior Publication Data

US 2014/0243878 A1 Aug. 28, 2014

(51) Int. Cl.
*A61M 29/00* (2006.01)
*A61F 2/01* (2006.01)

(52) U.S. Cl.
CPC .............. *A61F 2/01* (2013.01); *A61F 2002/011* (2013.01); *A61F 2002/016* (2013.01); *A61F 2230/008* (2013.01)

(58) Field of Classification Search
CPC ....................... A61B 17/7022; A61B 17/22031; A61F 2/82; A61F 2/01; A61F 2/011; A61F 2/013; A61F 2002/016
USPC .......... 606/200, 198, 123, 830, 831, 833, 843
See application file for complete search history.

(56) References Cited

U.S. PATENT DOCUMENTS

| | | | |
|---|---|---|---|
| 5,375,612 A | 12/1994 | Cottenceau et al. | |
| 5,941,896 A * | 8/1999 | Kerr | A61G 2/01 606/192 |
| 6,506,205 B2 | 1/2003 | Goldberg et al. | |
| 6,558,406 B2 | 5/2003 | Okada | |
| 6,575,996 B1 | 6/2003 | Denison et al. | |
| 6,616,680 B1 * | 9/2003 | Thielen | A61F 2/013 606/191 |
| 6,652,554 B1 * | 11/2003 | Wholey et al. | 606/200 |
| 6,676,683 B1 * | 1/2004 | Addis | 606/200 |
| 7,144,408 B2 | 12/2006 | Keegan et al. | |
| 7,220,271 B2 | 5/2007 | Clubb et al. | |
| 7,625,390 B2 | 12/2009 | Hendriksen et al. | |
| 7,763,044 B2 | 7/2010 | Inoue | |
| 7,799,049 B2 | 9/2010 | Ostrovsky et al. | |
| 7,922,741 B2 | 4/2011 | Gilson et al. | |
| 8,029,529 B1 * | 10/2011 | Chanduszko | 606/200 |
| 2007/0156170 A1 * | 7/2007 | Hancock et al. | 606/200 |
| 2007/0198028 A1 * | 8/2007 | Miloslavski | A61B 17/221 606/127 |
| 2008/0262532 A1 | 10/2008 | Martin | |
| 2009/0105747 A1 | 4/2009 | Chanduszko et al. | |
| 2009/0171441 A1 * | 7/2009 | Osborne | 623/1.15 |
| 2010/0030254 A1 | 2/2010 | Chanduszko et al. | |
| 2011/0040321 A1 * | 2/2011 | Cartier | 606/200 |
| 2011/0166593 A1 * | 7/2011 | Paul, Jr. | 606/200 |
| 2012/0172654 A1 * | 7/2012 | Bates | 600/16 |

* cited by examiner

*Primary Examiner* — Katherine M Shi
*Assistant Examiner* — Mohamed Gabr
(74) *Attorney, Agent, or Firm* — Brinks Gilson & Lione

(57) ABSTRACT

An intravascular filter configured for upstream or downstream retrieval and a method for retrieving an intravascular filter from a patient's vena cava through the patient's femoral vein. The filter includes a downstream hub, an upstream hub, a plurality of primary struts extending from the downstream hub to the upstream hub, a plurality of secondary struts extending upstream from fixed ends housed in the downstream hub to free ends, secondary strut eyelets disposed at the free ends of the secondary struts, a loop member disposed through the secondary strut eyelets, an upstream coupling element disposed with the upstream hub, and a tether extending from the loop member to the upstream coupling element.

20 Claims, 7 Drawing Sheets

CONICAL VENA CAVA FILTER WITH JUGULAR OR FEMORAL RETRIEVAL

BACKGROUND

The present invention relates to medical devices. More particularly, the invention relates to a removable intravascular filter that can be removed from the vena cava of a patient through the patient's jugular or femoral vein.

Filtering devices that are percutaneously placed in the vena cava have been available for a number of years. A need for such filtering devices arises in trauma patients, orthopedic surgery patients, neurosurgery patients, or in patients having medical conditions requiring bed rest or non-movement. Patients having such medical conditions face an increased risk of thrombosis in the peripheral vasculature, wherein thrombi break away from the vessel wall, risking downstream embolism or embolization. For example, depending on the size, such thrombi pose a serious risk of pulmonary embolism wherein blood clots migrate from the peripheral vasculature through the heart and into the lungs.

Historically, vena cava filters were considered to be permanent implants and remained implanted in the patient for life. More recently, removable vena cava filters have been developed. These filters may be removed from the patient's vena cava after the condition or medical problem that required the device has passed.

The benefits of vena cava filters, and particularly removable vena cava filters, have been well established, but improvements may be made. For example, the vast majority of the removable vena cava filters currently on the market must be removed through the patient's jugular vein. In some instances, however, removal through the patient's femoral vein is preferable to removal through the jugular vein. For example, filters sometimes shift or become stuck in a patient's vena cava. The ability to retrieve such troublesome filters from a different access point can increase the likelihood that they will be removed successfully. In addition, jugular retrieval requires that a retrieval sheath be advanced through the patient's heart, which is contraindicated in some cases. Finally, scarring at the access point is less noticeable when retrieval is initiated through the femoral vein.

It has been a challenge to design a vena cava filter suitable for removal through a patient's femoral vein.

SUMMARY OF INVENTION

The present invention generally provides an intravascular filter suitable for upstream or downstream retrieval. The invention also provides a method for retrieving an intravascular filter from a patient's vena cava through the patient's femoral vein.

In one embodiment, an intravascular filter configured for upstream retrieval is provided. The filter comprises a downstream hub and an upstream hub disposed along a longitudinal axis of the filter. The filter further comprises a plurality of primary struts having downstream and upstream ends. The downstream hub houses the downstream ends of the primary struts; the upstream hub houses the upstream ends of the primary struts. The filter further comprises a plurality of secondary struts having fixed and free ends. The downstream hub houses the fixed ends of the secondary struts. The secondary struts extend upstream from the downstream hub to the free ends. The free ends are disposed longitudinally between the downstream hub and the upstream hub. Each secondary strut has a secondary strut eyelet disposed at its free end. The filter further comprises a loop member disposed through the secondary strut eyelets. The filter further comprises a coupling element disposed with the upstream hub for upstream retrieval of the filter. A tether extends from the loop member to the upstream coupling element.

In another embodiment, a method for retrieving an intravascular filter from a patient's vena cava through the patient's femoral vein is provided. The method comprises percutaneously inserting a retrieval assembly comprising a retrieval sheath and a control member into the patient's vasculature through the patient's femoral vein. The method further comprises advancing the retrieval assembly through the patient's vasculature to a retrieval position proximal to the intravascular filter in the patient's vena cava. The filter comprises a downstream hub and an upstream hub disposed along a longitudinal axis of the filter. The filter further comprises a plurality of primary struts having downstream and upstream ends. The downstream hub houses the downstream ends of the primary struts; the upstream hub houses the upstream ends of the primary struts. The filter further comprises a plurality of secondary struts having fixed and free ends. The downstream hub houses the fixed ends of the secondary struts. The secondary struts extend upstream from the downstream hub to the free ends. The free ends are disposed longitudinally between the downstream hub and the upstream hub. Each secondary strut has a secondary strut eyelet disposed at its free end. The filter further comprises a loop member disposed through the secondary strut eyelets. The filter further comprises a coupling element disposed with the upstream hub for upstream retrieval of the filter. A tether extends from the loop member to the upstream coupling element. The method further comprises attaching the control member to the upstream coupling element of the intravascular filter and retracting the control member proximally through the retrieval sheath to apply tension to the upstream coupling element. The upstream coupling element relays the tension through the tether to the loop member to urge the secondary struts toward the longitudinal axis of the filter. The method further comprises advancing the retrieval sheath distally relative to the control member to place the retrieval sheath over the intravascular filter and removing the retrieval assembly and the intravascular filter from the patient's vasculature.

Further objects, features, and advantages of the present invention will become apparent from consideration of the following description and the appended claims when taken in connection with the accompanying drawings.

BRIEF DESCRIPTION OF THE DRAWINGS

FIG. 1b is a side view of the intravascular filter of FIG. 1a in a collapsed state in accordance with the principles of the present invention.

FIG. 2 is a cross-sectional view of the upstream hub of the intravascular filter of FIG. 1a.

FIG. 4 is an environmental view of the filter of FIG. 1a.

DETAILED DESCRIPTION

An intravascular filter configured for upstream or downstream retrieval is provided. The filter may be implanted in a patient's vena cava and may be removed from the vena cava through the patient's jugular or femoral vein. A method of removing an intravascular filter from a patient's vena cava through the patient's femoral vein is also provided.

As used herein, the terms "upstream" and "downstream" refer to the direction of blood flow in a patient's vasculature. When these terms are used to describe the elements of an intravascular filter, they suggest a preferred orientation of the filter in the patient's vasculature. However, these terms are not intended to be limiting in this regard. In other words, a filter otherwise including the structural elements recited herein will not be deemed to fall outside the scope of the present invention merely because it is implanted in a different orientation.

Figure 1A:
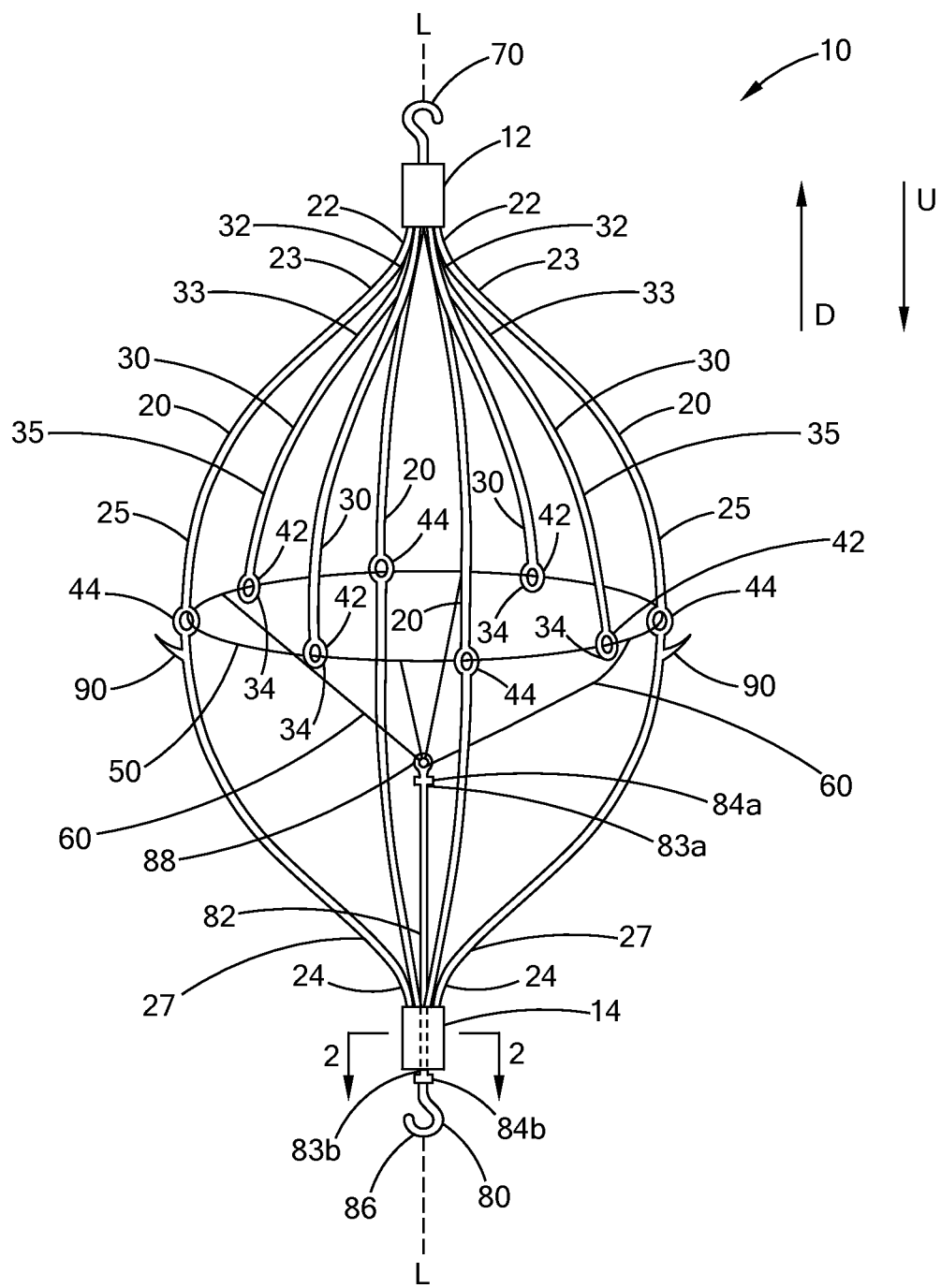
FIG. 1a is a side view of an intravascular filter in an expanded state in accordance with the principles of the present invention.
Figures 1B, 2:
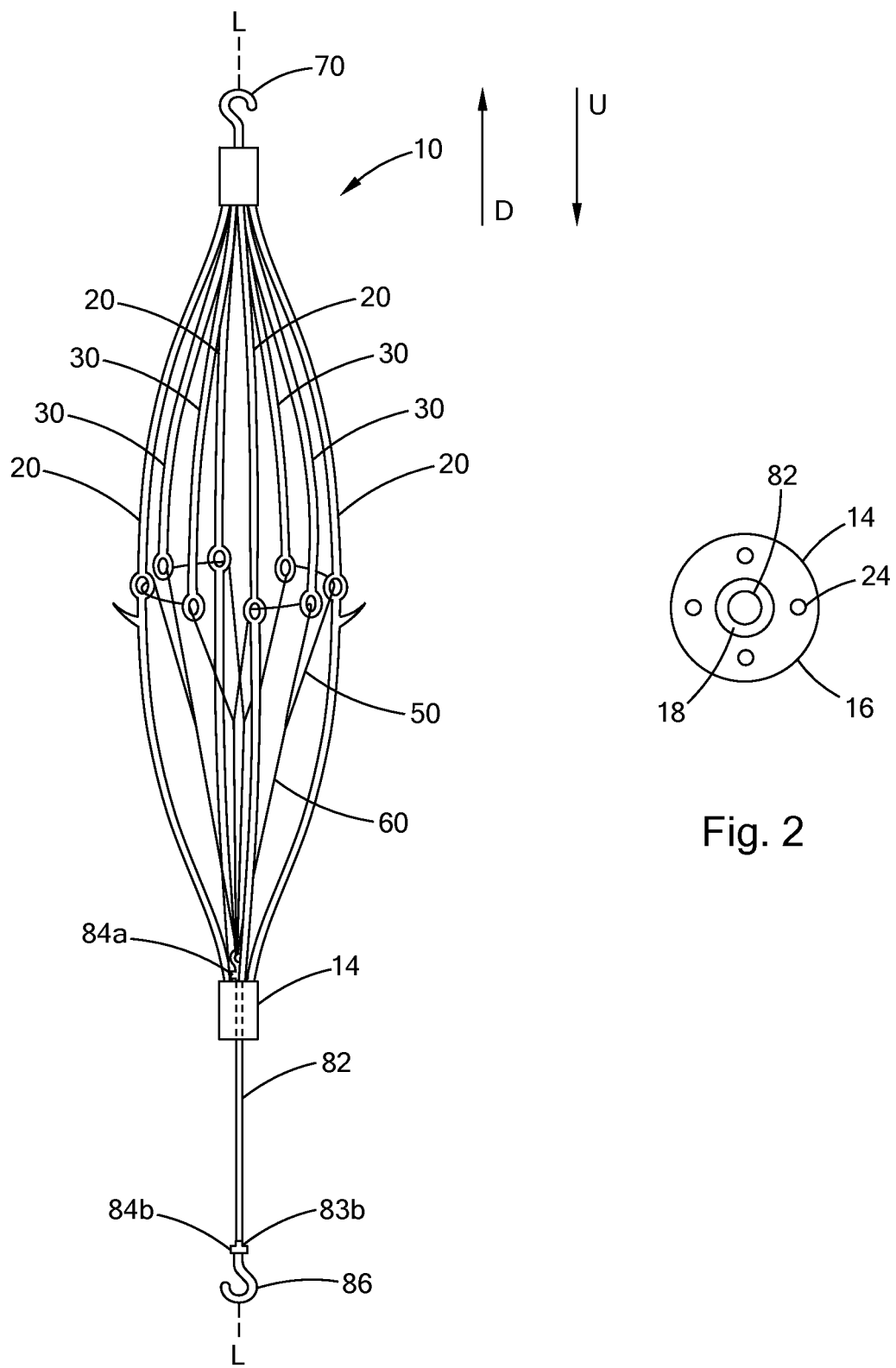

FIGS. 1a and 1b illustrate an intravascular filter 10 in accordance with the principles of the present invention. The filter 10 has an expanded configuration (FIG. 1a) suitable for capturing thrombi in a patient's blood vessel (e.g., in the patient's vena cava) and a collapsed configuration (FIG. 1b) suitable for removal from the patient's vasculature. In FIGS. 1a and 1b, the upstream direction is indicated by the arrow U, and the downstream direction is indicated by the arrow D.

The filter 10 comprises a downstream hub 12 and an upstream hub 14 disposed along a longitudinal axis L of the filter 10, a plurality of primary struts 20 extending from the downstream hub 12 to the upstream hub 14, a plurality of secondary struts 30 extending upstream from the downstream hub 12, a downstream coupling element 70 disposed with the downstream hub 12 for downstream removal of the filter 10, and an upstream coupling element 80 disposed with the upstream hub 14 for upstream removal of the filter 10.

The filter 10 may have any suitable number and configuration of primary and secondary struts 20 and 30 without falling beyond the scope of the present invention. In one embodiment, shown in FIG. 1a, the filter 10 has a plurality of primary struts 20 and a plurality of secondary struts 30 freely spaced between the primary struts 30. For example, the filter 10 preferably has between two and eight primary struts 20, more preferably between three and six primary struts 20, and most preferably four primary struts 20. The filter 10 preferably has between two and sixteen secondary struts 30, more preferably between four and eight secondary struts 30, and most preferably either four or eight secondary struts 30.

In the embodiment shown in FIG. 1a, the filter 10 has four primary struts 20 and four secondary struts 30. Each primary strut 20 has a downstream end 22, a downstream portion 23, a middle portion 25, and upstream portion 27, and an upstream end 24. The downstream hub 12 houses the downstream ends 22 of the primary struts 20. Each primary strut 20 extends arcuately in a longitudinal plane including the longitudinal axis L. When the filter 10 is in the expanded state, as shown in FIG. 1a, the downstream portion 23 extends upstream from the downstream end 22 and bends away from the longitudinal axis L, the middle portion 25 extends upstream from the downstream portion 23 and bends toward the longitudinal axis L, and the upstream portion 27 extends upstream from the middle portion 25 and bends away from the longitudinal axis L to the upstream end 24. The upstream hub 14 houses the upstream ends 24 of the primary struts 20.

In the embodiment shown in FIG. 1a, each secondary strut 30 has a fixed end 32, a first portion 33, a second portion 35, and a free end 34. The downstream hub 12 houses the fixed ends 32 of the secondary struts 30. Each secondary strut 30 extends arcuately in a longitudinal plane including the longitudinal axis L. When the filter 10 is in the expanded state, as shown in FIG. 1a, the first portion 33 extends upstream from the fixed end 32 and bends away from the longitudinal axis L, and the second portion 35 extends upstream from the first portion 33 and bends toward the longitudinal axis L to the free end 34.

Preferably, the primary and secondary struts 20 and 30 are formed from a superelastic material, stainless steel wire, nickel-titanium alloy (e.g., Nitinol), cobalt-chromium-nickel-molybdenum-iron alloy, cobalt-chrome alloy, or any other suitable material that will result in a self-opening or self-expanding filter.

The free ends 34 of the secondary struts 30 are disposed longitudinally between the downstream hub 12 and the upstream hub 14. In the filter 10 shown in FIG. 1a, the free ends 34 of the secondary struts 30 define a plane (not shown) approximately bisecting the longitudinal axis L between the downstream hub 12 and the upstream hub 14. The plane defined by the free ends 34 of the secondary struts 30 is approximately perpendicular to the longitudinal axis L. In other embodiments, the free ends 34 of the secondary struts 30 may define a plane intersecting the longitudinal axis L at a point closer to the downstream hub 12 or at a point closer to the upstream hub 14. The plane defined by the free ends 34 of the secondary struts 30 may be approximately perpendicular to the longitudinal axis L, or such plane may intersect the longitudinal axis L at a non-right angle. In still other embodiments, the free ends 34 of the secondary struts 30 may not define a single plane.

Each secondary strut 30 has a secondary strut eyelet 42 disposed at its free end 34. In the filter 10 shown in FIGS. 1a and 1b, the secondary strut eyelets 42 are unitarily formed with the secondary struts 30. In other embodiments, the secondary strut eyelets 42 may be fixedly attached to the free ends 34 of the secondary struts 30, e.g. by welding or by adhesive bonding.

In the filter 10 shown in FIG. 1a, each primary strut 20 has a primary strut eyelet 44 disposed in its middle portion 25. Like the secondary strut eyelets 42, the primary strut eyelets 44 may be unitarily formed with the primary struts 20 (as shown in FIGS. 1a and 1b) or may be fixedly attached to the primary struts 20. In other embodiments, the primary struts 20 do not have primary strut eyelets 44.

The primary strut eyelets 44 may be disposed about evenly with the secondary strut eyelets 42 along the longitudinal axis L of the filter 10. Since the secondary strut eyelets 44 are disposed at the free ends 34 of the secondary struts 30, the primary strut eyelets 44 may be disposed about evenly with the free ends 34 of the secondary struts 30. For example, if the free ends 34 of the secondary struts 30 define a plane approximately bisecting the longitudinal axis L between the downstream hub 12 and the upstream hub 14, the primary strut eyelets 44 may lie in the same plane. In other embodiments, the primary strut eyelets 44 may lie in a plane defined by the free ends 34 of the secondary struts that intersects the longitudinal axis L at a point closer to the downstream hub 12 or at a point closer to the upstream hub 14. In other embodiments, the primary strut eyelets 44 may not lie in the same plane as the secondary strut eyelets 42.

In some embodiments, at least one of the primary or secondary struts 20 or 30 further comprises an anchoring hook 90 extending away from the longitudinal axis L and downstream to engage a blood vessel wall and prevent downstream migration of the filter 10. As shown in FIGS. 1a and 1b, the anchoring hooks 90 may be disposed in the middle portions 25 of one or more of the primary struts 20. Where the primary struts 20 include primary strut eyelets 44, the anchoring hooks 90 may be disposed upstream or downstream of the primary strut eyelets 44. In other embodiments, the anchoring hooks 90 may extend from the primary strut eyelets 44.

The filter 10 further comprises a loop member 50 disposed through the primary and secondary strut eyelets 44 and 42. In other embodiments, including embodiments in which the primary struts 20 do not include primary strut eyelets 44, the loop member 50 is only disposed through the secondary strut eyelets 42.

The loop member may be formed from one or more strands of any material that is suitably flexible to slide through the primary and secondary strut eyelets 44 and 42. For example, the loop member may be formed from a fine metal wire, such as stainless steel wire. Alternatively, the loop member may be formed from a synthetic material, such as nylon, polyethylene, polypropylene, a polyester (e.g., polyethylene terephthalate), polyetherurethane urea, or a fluorinated polymer (e.g., polytetrafluoroethylene). As used herein, the term "loop member" includes both a "closed loop" and an "open loop."

In the filter 10 shown in FIGS. 1a and 1b, the loop member 50 is a closed loop. As used herein, the term "closed loop" includes an elongate member initially formed as a closed loop as well as a member formed into a closed loop by fixedly attaching the opposing ends of the member. The loop member 50 passes sequentially through adjacent primary and secondary strut eyelets 44 and 42, such that the loop member 50 extends around the circumference of the filter 10 when the filter 10 is in the expanded configuration (FIG. 1a).

As shown in FIGS. 1a and 1b, the loop member 50 is slidably disposed through all of the primary and secondary strut eyelets 44 and 42. In other embodiments, however, the loop member 50 may be fixedly attached to one or more of the primary and secondary strut eyelets 44 and 42. For example, the loop member 50 may be tied to one or more of the primary and secondary strut eyelets 44 and 42, or it may be adhesively bonded to such eyelets. The primary and/or secondary strut eyelets 44 and/or 42 to which the loop member 50 is fixedly attached may be known as first eyelets, and the primary and/or secondary strut eyelets 44 and/or 42 through which the loop member 50 is slidably disposed may be known as second eyelets.

Figure 3A:
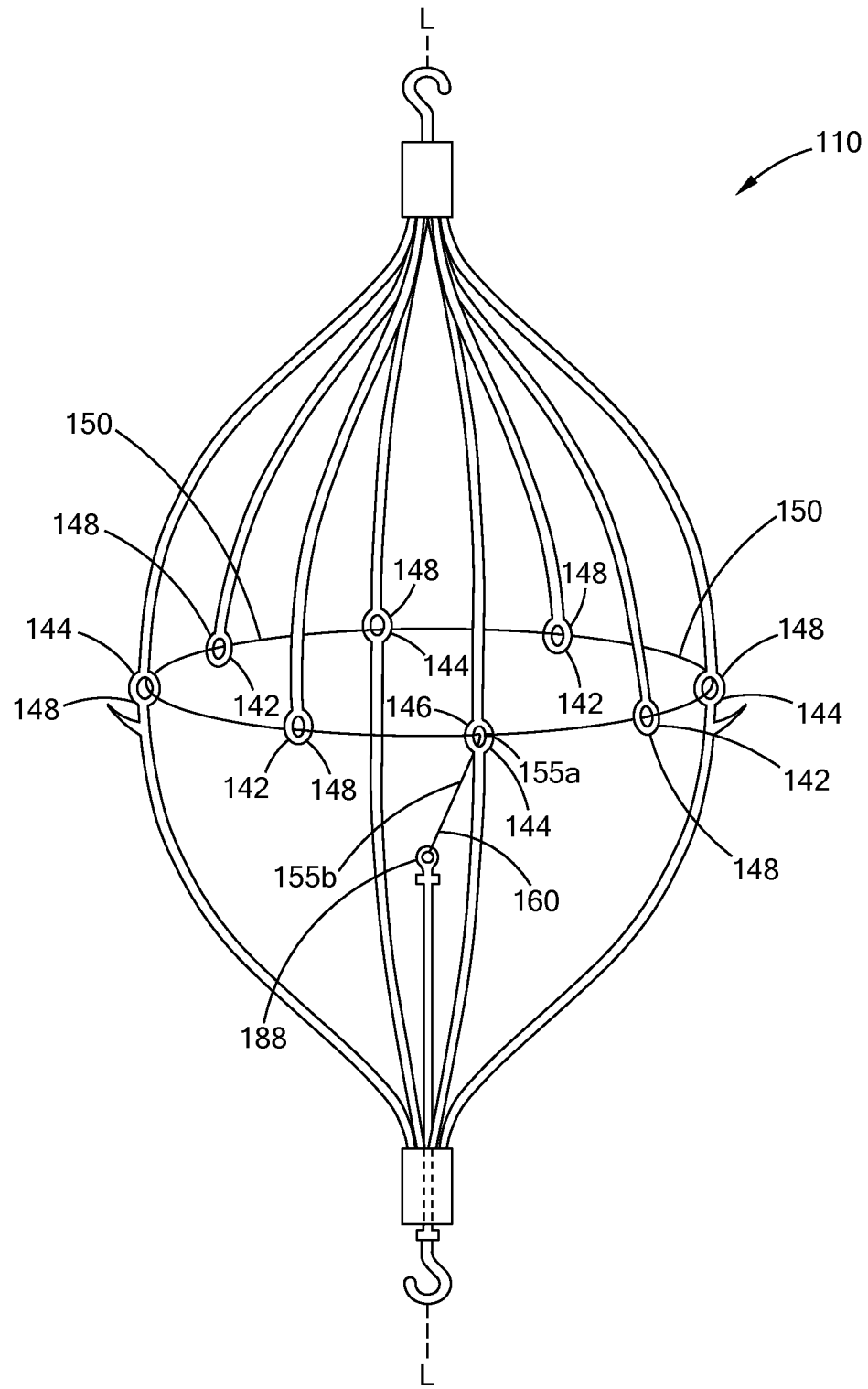
FIGS. 3a and 3b are partial side views of intravascular filters in accordance with other embodiments of the present invention.
Figure 3B:
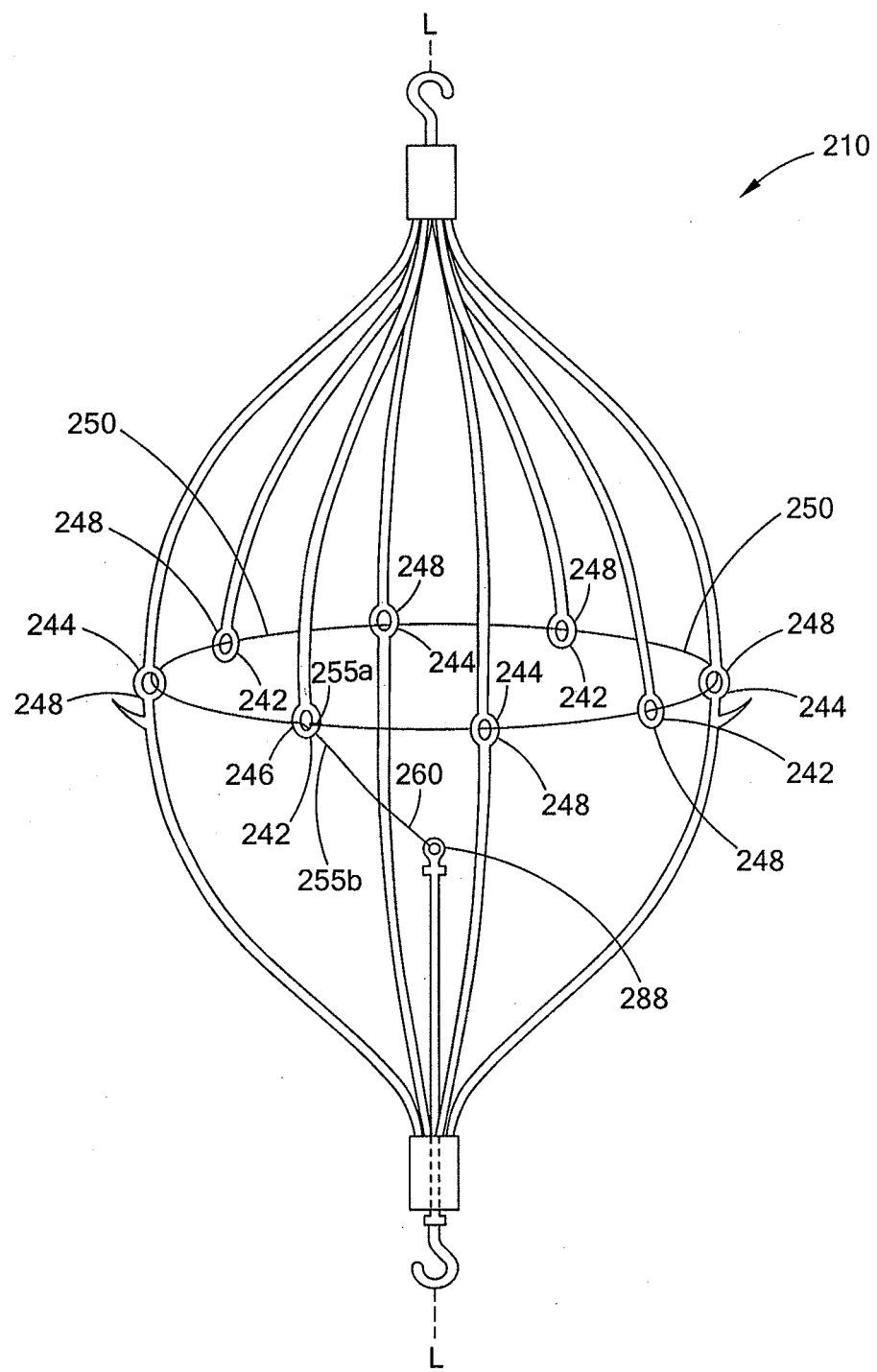

In other embodiments, shown in FIGS. 3a and 3b, the loop members 150 and 250 are open loops having attached ends 155a and 255a and unattached ends 155b and 255b. The attached end 155a or 255a is fixedly attached to a first eyelet 146 or 246, which may be a primary strut eyelet 144 (FIG. 3a) or a secondary strut eyelet 242 (FIG. 3b). The loop member 150 or 250 passes sequentially through adjacent second eyelets 148 or 248, including primary and secondary strut eyelets 144 or 244 and 142 or 242 around the circumference of the filter, and through the first eyelet 146 or 246, to define the loop.

Referring again to FIGS. 1a and 1b, the upstream coupling element 80 preferably is free to move longitudinally relative to the upstream hub 14. FIG. 2 depicts a cross-sectional view of the upstream hub 14. As shown in FIG. 2, the upstream hub 14 has an annular portion 16 defining an opening 18. The opening 18 is disposed along the longitudinal axis of the filter. The annular portion 16 houses the upstream ends 24 of the primary struts.

Referring again to FIGS. 1a and 1b, the upstream coupling element 80 comprises a longitudinal guide member 82, an attachment member 86, and a tether attachment 88. The longitudinal guide member 82 is slidably disposed through the opening 18 of the upstream hub 14. The longitudinal guide member 82 has a first end 83a disposed downstream of the upstream hub 14 and a second end 83b disposed upstream of the upstream hub 14. The attachment member 86 is disposed at the second end 83b of the longitudinal guide member 82. The tether attachment 88 is disposed at the first end 83a of the longitudinal guide member 82.

As shown in FIGS. 1a and 1b, the upstream coupling element 80 further comprises a first end stop 84a and a second end stop 84b disposed at the first and second ends 83a and 83b of the longitudinal guide member 82. The widths of the first and second end stops 84a and 84b are preferably greater than the diameter of the opening 18, such that the upstream coupling element 80 does not slide completely through the upstream hub 14.

As shown in FIGS. 1a and 1b, the filter 10 further comprises one or more tethers 60 extending from the loop member 50 to the upstream coupling element 80. More specifically, the tether(s) 60 attach to tether attachment 88 at the first end 83a of the longitudinal guide member 82 of the upstream coupling element 80. The filter 10 may include one tether 60 or a plurality of tethers 60. The tether(s) 60 may be formed from the same material as the loop member 50 or from any other suitable material.

When the loop member 50 is a closed loop, as shown in FIGS. 1a and 1b, the tether(s) 60 extend from one or more locations along the loop member 50 to the tether attachment 88. In this embodiment, the filter 10 preferably includes a plurality of tethers 60. For example the filter 10 may include two to ten tethers 60, preferably three to eight tethers 60, more preferably four to six tethers 60, and most preferably four tethers 60. The tethers 60 may be evenly or unevenly spaced along the loop member 50.

The embodiments shown in FIGS. 3a and 3b, where the loop members 150 and 250 are open loops, preferably include single tethers 160 and 260. The tethers 160 and 260 extend from the unattached ends 155b and 255b of the loop members 150 and 250 to the tether attachments 188 and 288. The unattached ends 155b and 255b of the loop members 150 and 250 are integrally connected with the tethers 160 and 260. The unattached ends 155b and 255b are understood to be "integrally connected" with the tethers 160 and 260 if the loop members 150 and 250 are unitarily formed with the tethers 160 and 260 or if the unattached ends 155b and 255b of the loop members 150 and 250 are fixedly attached to the downstream ends of the tethers 160 and 260 (e.g., by tying or by adhesive bonding).

In the following discussion of the deployment and retrieval of the filter 10, the terms "proximal" and "distal," and derivatives thereof, will be understood in the frame of reference of the medial practitioner deploying or retrieving the filter 10. Thus, "proximal" refers to locations closer to the practitioner, and "distal" refers to locations further from the practitioner (i.e., deeper in the patient's vasculature).

The filter 10 shown in FIG. 1a may be delivered to a patient's blood vessel, such as the patient's vena cava, using standard techniques familiar to those having ordinary skill in the relevant art. For example, a delivery system may be percutaneously inserted into the patient's vasculature via any suitable access site, such as the jugular vein, femoral vein, or any other suitable access site. The delivery system may be advanced through the patient's vasculature until the distal end of the delivery system is disposed in the patient's blood vessel at the desired site of deployment, e.g., in the patient's vena cava.

If the filter 10 is to be deployed in the vena cava, and the delivery system is inserted into the patient's vasculature through the patient's jugular vein, the filter 10 is inserted into the body with the upstream hub 14 leading and the downstream hub 12 trailing. By contrast, if the delivery system is inserted into the patient's vasculature through the patient's femoral vein, the filter 10 is inserted into the body with the downstream hub 12 leading and the upstream hub 14 trailing.

Upon deployment from the distal end of the delivery system, the struts of the filter preferably self-expand away from the longitudinal axis until the struts engage the blood vessel walls. While the foregoing method is provided by way of example, a person having ordinary skill in the relevant art will understand that a filter constructed in accordance with the principles of the present invention may be deployed using any other suitable technique without falling outside the scope of the present invention.

Figure 4:
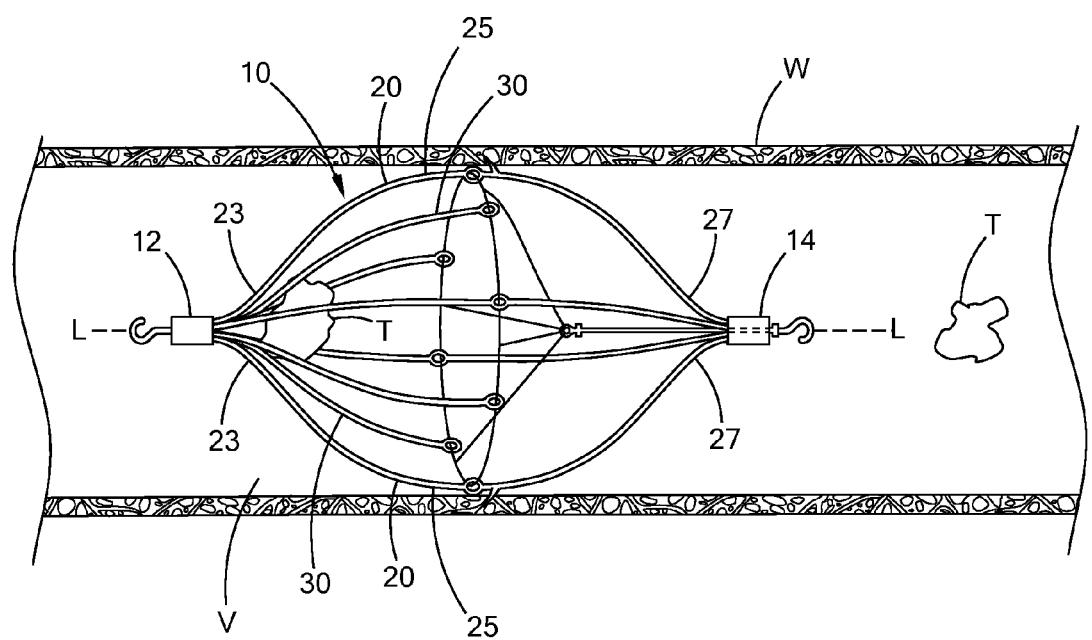
Figure 5:
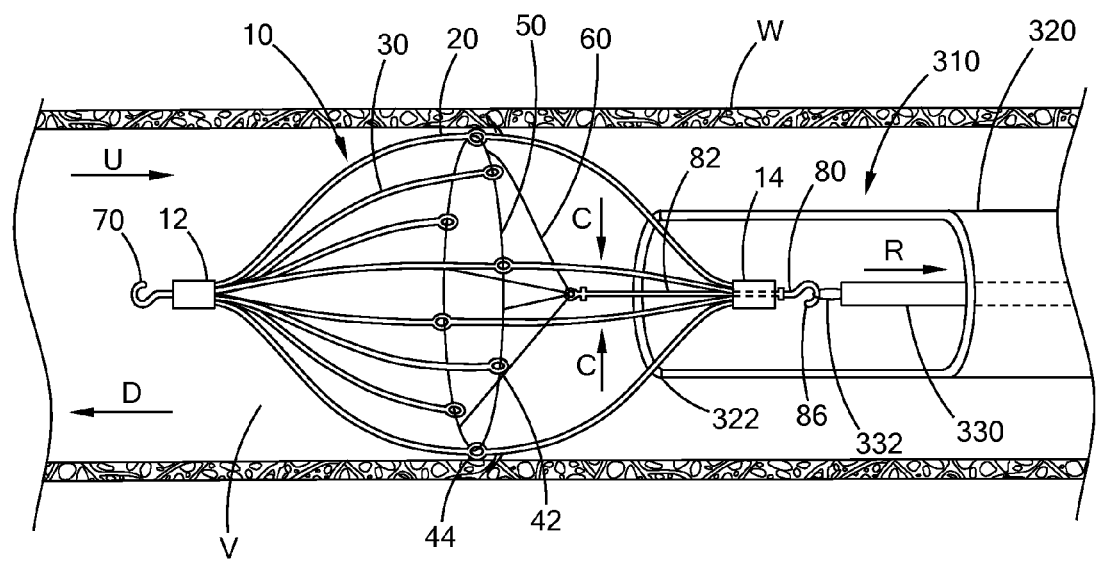
FIG. 5 is an environmental view of a retrieval assembly and the filter of FIG. 1a in which a control member of the retrieval assembly is attached to the upstream coupling element of the filter during retrieval.

The operation and retrieval of the filter 10 will now be described with reference to FIGS. 4-6. When the filter 10 is deployed in a patient's blood vessel V, the primary and secondary struts 20 and 30 engage the walls W of the blood vessel V, anchoring and centering the filter 10 in the blood vessel V.

Thrombi T carried by the blood stream are captured in the filter 10. More specifically, the thrombi T are captured along the longitudinal axis of the filter 10 near the downstream hub 12 of the filter 10. As the thrombi T enter the filter 10, the thrombi T are funneled toward the longitudinal axis L of the filter 10 by the primary and secondary struts 20 and 30. Several structural features of the filter 10 facilitate this funneling action. First, because the secondary struts 30 do not extend all the way to the upstream hub 14 of the filter 10, the thrombi T are able to pass between the upstream portions 27 of the primary struts 20 into the inside of the filter 10. In addition, the upstream portion 27 (and any part of the middle portion 25 upstream of the primary strut eyelet 44) of each primary strut 20 preferably has a smaller diameter than the downstream portion 23 (and any part of the middle portion 25 downstream of the primary strut eyelet 44) of the primary strut 20, further facilitating the passage of thrombi T into the inside of the filter 10. Second, the angle of the downstream and middle portions 23 and 25 of the primary struts 20, and the angle of the secondary struts 30, relative to the longitudinal axis L causes the thrombi T to slide toward the longitudinal axis as the flow of blood pushes the thrombi T downstream.

The capture of thrombi T along the longitudinal axis L of the filter 10 is advantageous for several reasons. First, because blood flow is greatest near the center of the blood vessel V, thrombi T captured near the center of the vessel are more likely to dissolve after capture. Second, thrombi T captured along the wall of the blood vessel V tend to grow by accumulating additional clot material, and can eventually occlude the vessel.

After the risk of embolism has subsided, the filter 10 may be removed from the blood vessel V through either the patient's jugular vein or femoral vein. The filter 10 may be removed through the patient's jugular vein using procedures that are well known to those having ordinary skill in the relevant art. For example, the filter 10 may be removed through the patient's jugular vein using the method described in U.S. Pat. No. 7,625,390, the entire contents of which are incorporated herein by reference.

Alternatively, the filter 10 may be removed through the patient's femoral vein. Referring now to FIG. 5, removal of the filter 10 is initiated by inserting a retrieval assembly 310 into the patient's vasculature through the patient's femoral vein. The retrieval assembly includes a retrieval sheath 320 and a first control member 330. The first control member 330 has a snare 332 disposed at its distal end.

Referring again to FIG. 5, the retrieval assembly 310 is advanced through the patient's vasculature to a position immediately upstream of the filter 10 in the patient's blood vessel V. The first control member 330 is advanced from the lumen of the retrieval sheath 320, and the snare 332 is attached to the attachment member 86 of the upstream coupling element 80. The first control member 330 is then retracted in the direction of the arrow R, applying tension to the attachment member 86.

As tension is applied to the attachment member 86 by the retraction of the first control member 330, the longitudinal guide member 82 slides in an upstream direction through the upstream hub 14, applying tension to the tethers 60. The tethers 60, in turn, apply tension to the loop member 50, causing the loop member 50 to slide through the primary and secondary strut eyelets 44 and 42.

As the loop member 50 slides through the primary and secondary strut eyelets 44 and 42, the circumference of the loop member 50 decreases. The loop member 50 functions like a "drawstring," pulling the primary and secondary struts 20 and 30 toward the longitudinal axis of the filter 10 and the blood vessel V such that the filter collapses as indicated by the arrows C.

Figure 6:
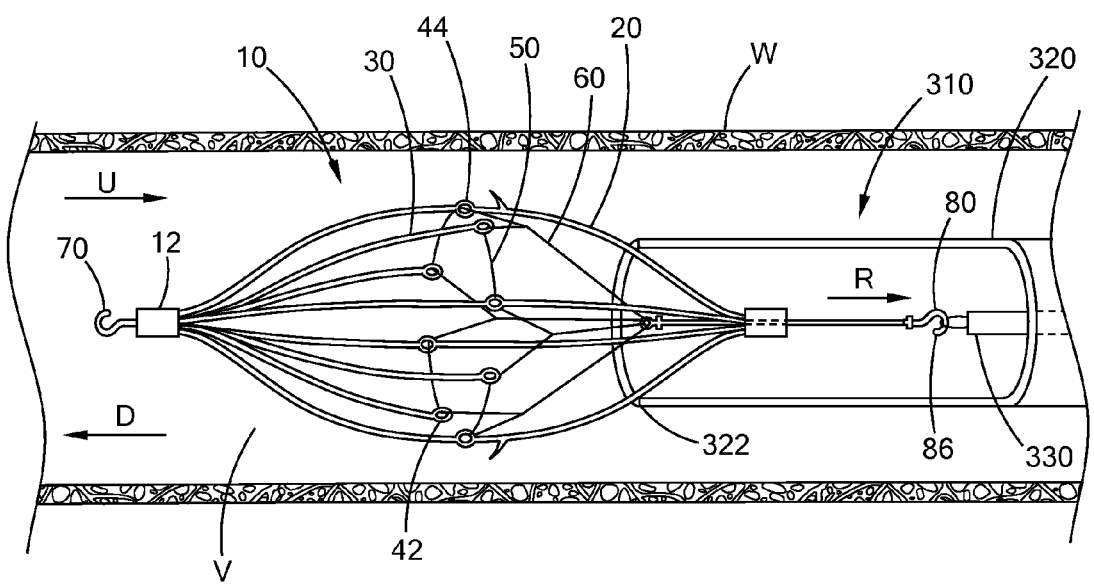
FIG. 6 is an environmental view of a retrieval assembly and the filter of FIG. 1a in which the filter has been moved to a partially collapsed state by applying tension to the upstream coupling element of the filter.

FIG. 6 depicts the filter 10 in a partially collapsed configuration. Upon further retraction of the first control member 330, additional tension is applied to the tethers 60 and the loop member 50, resulting in further collapse of the filter 10 until the filter 10 assumes the collapsed configuration as shown in FIG. 1b. In the collapsed configuration, the filter 10 can be accommodated in the lumen of the retrieval sheath 320.

As the struts 20 and 30 disengage the wall W of the blood vessel V, the filter 10 tends to move proximally due to the tension applied to the attachment member 86. To hold the filter 10 in position, the medical practitioner may brace the distal end 322 of the retrieval sheath 320 against the primary struts 20 as shown in FIGS. 5 and 6. The medical practitioner may also employ a second control member (not shown) to hold the filter 10 in position. The second control member may be introduced into the patient's vasculature through the retrieval sheath 320 and may brace against the upstream side of the downstream hub 12. Alternatively, the second control member may be introduced into the patient's vasculature through the patient's jugular vein and attach to the downstream coupling element 70.

As will be apparent from the foregoing discussion, the loop member 50, tethers 60, and upstream coupling element 80 are important to the femoral vein retrieval of the filter 10. Using this mechanism, the secondary struts 30 are collapsed to a diameter smaller than the diameter of the retrieval sheath 320, such that the filter 10 can be pulled into the lumen of the sheath 320. Once the filter 10 is stowed in the lumen of the retrieval sheath 320, the retrieval assembly 310 and the filter 10 may be removed from the patient's vasculature. A similar procedure may be employed for retrieving the filters 110 and 210 depicted in FIGS. 3a and 3b.

Figure 7:
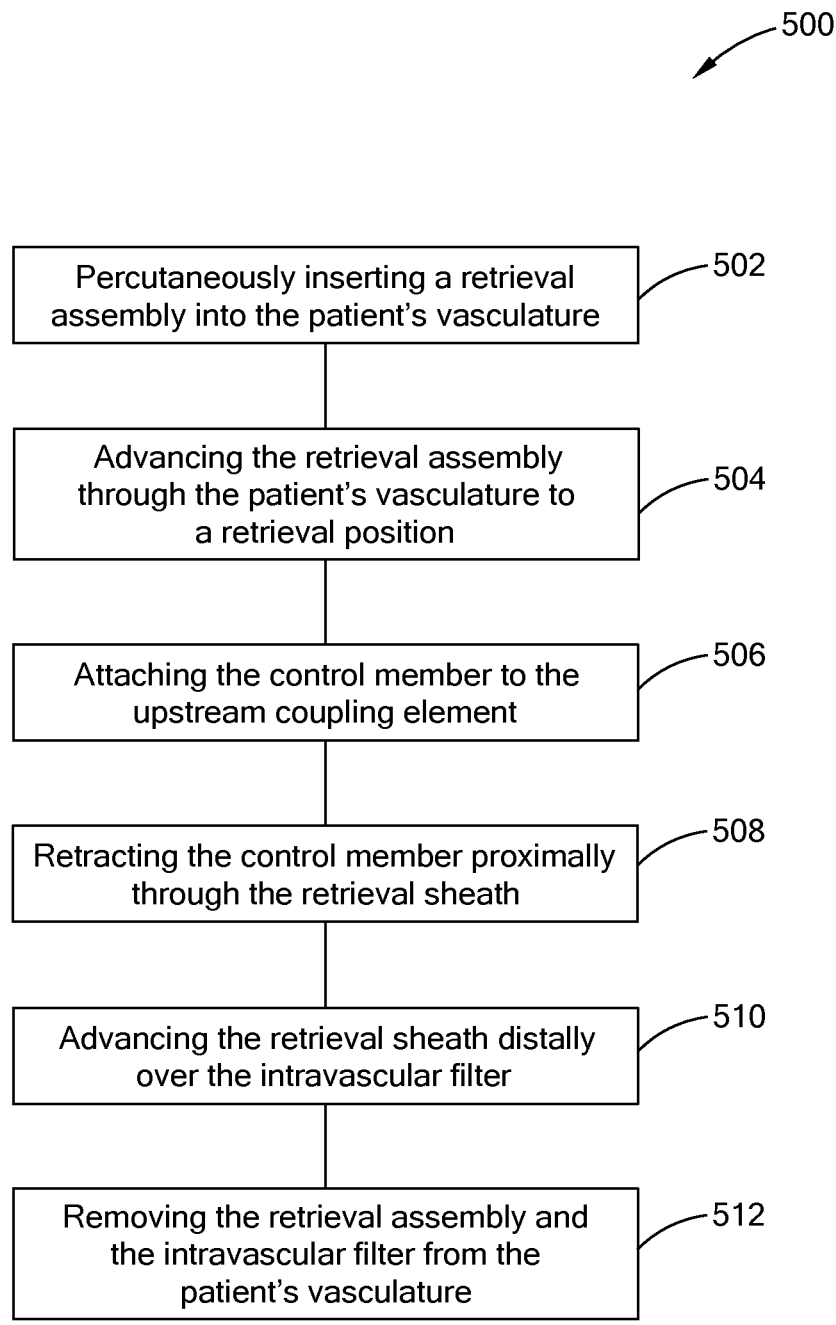
FIG. 7 is a flow chart depicting a method for retrieving an intravascular filter from a patient's vena cave through the patient's femoral vein.

Referring now to FIG. 7, a method for retrieving an intravascular filter, such as the filter 10, from a patient's vena cava through the patient's femoral vein is provided. As indicated in box 502, the method 500 involves percutaneously inserting a retrieval assembly, such as the retrieval assembly 310, into the patient's vasculature through the patient's femoral vein. The retrieval assembly comprises a retrieval sheath and a first control member.

As indicated in box 504, the method 500 further comprises advancing the retrieval assembly through the patient's vasculature to a retrieval position proximal to the intravascular filter in the patient's vena cava. The first control member is then attached to the upstream coupling element of the intravascular filter, as indicated in box 506.

As indicated in box 508, the method 500 further comprises retracting the first control member proximally through the retrieval sheath to apply tension to the upstream coupling element. The distal end of the retrieval sheath may be braced against the primary struts of the filter to hold the filter in position during the retraction of the first control member. The upstream coupling element relays the tension through the tether to the loop member to urge the secondary struts toward the longitudinal axis of the filter. The retraction of the control member may cause a portion of the loop member to slide through at least one of the secondary strut eyelets.

Once the filter is in a collapsed configuration, the retrieval sheath is advanced distally relative to the first control member to place the retrieval sheath over the intravascular filter (box 510). With the filter stowed in the lumen of the retrieval sheath, the retrieval assembly and the intravascular filter are removed from the patient's vasculature (box 512).

While the present invention has been described in terms of certain preferred embodiments, it will be understood that the invention is not limited to the disclosed embodiments, as those having skill in the art may make various modifications without departing from the scope of the following claims.

What is claimed is:

1. An intravascular filter configured for upstream retrieval, the filter comprising:
    a downstream hub and an upstream hub disposed along a longitudinal axis of the filter;
    a plurality of primary struts having downstream and upstream ends, the downstream hub housing the downstream ends of the primary struts, the upstream hub housing the upstream ends of the primary struts;
    a plurality of secondary struts having fixed and free ends, the downstream hub housing the fixed ends of the secondary struts, the secondary struts extending upstream from the downstream hub to the free ends, the free ends being disposed longitudinally between the downstream hub and the upstream hub, each secondary strut having a secondary strut eyelet disposed at its free end;
    a loop member disposed through the secondary strut eyelets;
    an upstream coupling element extending from a first end to a second end, the first end spaced apart from and terminating upstream of the downstream hub, the second end disposed adjacent the upstream hub, the upstream coupling element disposed with the upstream hub for upstream retrieval of the filter; and a tether directly connected to the loop member and extending to the upstream coupling element.

2. The intravascular filter of claim 1, wherein each primary strut has a primary strut eyelet disposed between its downstream and upstream ends; and wherein the loop member is disposed through the primary strut eyelets.

3. The intravascular filter of claim 2, wherein the primary strut eyelets are disposed about evenly with the secondary strut eyelets along the longitudinal axis of the filter.

4. The intravascular filter of claim 2, wherein the primary strut eyelets and secondary strut eyelets collectively include one first eyelet and one or more second eyelets, the loop member being fixedly attached to the first eyelet and slidably disposed through the second eyelets.

5. The intravascular filter of claim 4, wherein the first eyelet is a primary strut eyelet.

6. The intravascular filter of claim 4, wherein the first eyelet is a secondary strut eyelet.

7. The intravascular filter of claim 4, wherein the loop member is an open loop having an attached end and an unattached end, the attached end of the loop member being fixedly attached to the first eyelet, the unattached end being integrally connected with the tether.

8. The intravascular filter of claim 1, wherein the upstream coupling element is free to move longitudinally relative to the upstream hub.

9. The intravascular filter of claim 8, wherein the upstream hub has an annular portion, the annular portion defining an opening along the longitudinal axis of the filter; and
    wherein the upstream coupling element comprises: a longitudinal guide member disposed through the opening of the upstream hub; and
    an attachment member;
    the longitudinal guide member having a first end disposed downstream of the upstream hub and a second end disposed upstream of the upstream hub,
    the attachment member being disposed at the second end of the longitudinal guide member.

10. The intravascular filter of claim 9, wherein the tether extends from the loop member to the first end of the longitudinal guide member.

11. The intravascular filter of claim 1, wherein the filter comprises a plurality of tethers.

12. The intravascular filter of claim 1, wherein one secondary strut eyelet is a first eyelet and one or more of the other secondary strut eyelets are second eyelets, the loop member being fixedly attached to the first eyelet and slidably disposed through the second eyelets.

13. The intravascular filter of claim 12, wherein the loop member is an open loop having an attached end and an unattached end, the attached end of the loop member being fixedly attached to the first eyelet, the unattached end being integrally connected with the tether.

14. The intravascular filter of claim 1, wherein the loop member is a closed loop.

15. The intravascular filter of claim 1, wherein at least one of the primary or secondary struts further comprises an anchoring hook, the anchoring hook extending away from the longitudinal axis and downstream to engage a blood vessel wall and prevent downstream migration of the filter.

16. The intravascular filter of claim 1, further comprising a downstream coupling element disposed with the downstream hub for downstream retrieval of the filter.

17. A method for retrieving an intravascular filter from a patient's vena cava through the patient's femoral vein, the method comprising:
    percutaneously inserting a retrieval assembly into the patient's vasculature through the patient's femoral vein, the retrieval assembly comprising a retrieval sheath and a first control member;
    advancing the retrieval assembly through the patient's vasculature to a retrieval position proximal to the intravascular filter in the patient's vena cava, the intravascular filter comprising:
        a downstream hub and an upstream hub disposed along a longitudinal axis of the filter;

a plurality of primary struts having downstream and upstream ends, the downstream hub housing the downstream ends of the primary struts, the upstream hub housing the upstream ends of the primary struts;

a plurality of secondary struts having fixed and free ends, the downstream hub housing the fixed ends of the secondary struts, the secondary struts extending upstream from the downstream hub to the free ends, the free ends being disposed longitudinally between the downstream hub and the upstream hub, each secondary strut having a secondary strut eyelet disposed at its free end;

a loop member disposed through the secondary strut eyelets;

an upstream coupling element extending from a first end to a second end, the first end spaced apart from and terminating upstream of the downstream hub, the second end disposed adjacent the upstream hub, the upstream coupling element disposed with the upstream hub for upstream retrieval of the filter;

a tether directly connected to the loop member and extending to the upstream coupling element;

attaching the first control member to the upstream coupling element of the intravascular filter;

retracting the first control member proximally through the retrieval sheath to apply tension to the upstream coupling element, the upstream coupling element relaying the tension through the tether to the loop member to urge the secondary struts toward the longitudinal axis of the filter;

advancing the retrieval sheath distally relative to the first control member to place the retrieval sheath over the intravascular filter; and removing the retrieval assembly and the intravascular filter from the patient's vasculature.

18. The method of claim 17, wherein said retracting the first control member causes a portion of the loop member to slide through at least one of the secondary strut eyelets.

19. The method of claim 17, wherein the retrieval sheath has a proximal end and a distal end; and wherein the method further comprises bracing the distal end of the retrieval sheath against the primary struts of the filter while retracting the control member.

20. An intravascular filter configured for upstream retrieval, the filter comprising:

a downstream hub and an upstream hub disposed along a longitudinal axis of the filter;

a plurality of primary struts having downstream and upstream ends, the downstream hub housing the downstream ends of the primary struts, the upstream hub housing the upstream ends of the primary struts;

a plurality of secondary struts having fixed and free ends, the downstream hub housing the fixed ends of the secondary struts, the secondary struts extending upstream from the downstream hub to the free ends, the free ends being disposed longitudinally between the downstream hub and the upstream hub, each secondary strut having a secondary strut eyelet disposed at its free end, one secondary strut eyelet being a first eyelet and one or more of the other secondary strut eyelets are second eyelets;

a loop member disposed through the secondary strut eyelets and fixedly attached to the first eyelet, the loop member being slidably disposed through the second eyelets, the loop member comprising an open loop having an attached end fixedly attached to the first eyelet and an unattached end;

an upstream coupling element extending from a first end to a second end, the first end spaced apart from and terminating upstream of the downstream hub, the second end disposed adjacent the upstream hub, the upstream coupling element disposed with the upstream hub for upstream retrieval of the filter; and a tether extending from the loop member to the upstream coupling element integrally connected with the unattached end.

* * * * *